(12) United States Patent
Kim et al.

(10) Patent No.: US 9,880,136 B2
(45) Date of Patent: Jan. 30, 2018

(54) METHOD FOR AUTOMATIC IN VITRO DIAGNOSIS

(71) Applicant: BODITECHMED. INC, Chuncheon-si, Gangwon-do (KR)

(72) Inventors: Byeongchul Kim, Chuncheon-si (KR); Bongseok Mun, Namyangju-si (KR); Yeonghang Lee, Seoul (KR); Gwangwon Choi, Chuncheon-si (KR)

(73) Assignee: BODITECHMED, INC, Chuncheon-si, Gangwon-Do (KR)

( * ) Notice: Subject to any disclaimer, the term of this patent is extended or adjusted under 35 U.S.C. 154(b) by 142 days.

(21) Appl. No.: 15/037,330

(22) PCT Filed: Oct. 1, 2014

(86) PCT No.: PCT/KR2014/009282
§ 371 (c)(1),
(2) Date: May 18, 2016

(87) PCT Pub. No.: WO2015/072663
PCT Pub. Date: May 21, 2015

(65) Prior Publication Data
US 2016/0290975 A1    Oct. 6, 2016

(30) Foreign Application Priority Data
Nov. 18, 2013  (KR) .................. 10-2013-0140186

(51) Int. Cl.
*G01N 35/00* (2006.01)
*G01N 35/10* (2006.01)
(Continued)

(52) U.S. Cl.
CPC ............. *G01N 30/74* (2013.01); *G01N 33/48* (2013.01); *G01N 35/00029* (2013.01);
(Continued)

(58) Field of Classification Search
CPC .......... G01N 2035/00108; G01N 2035/00891; G01N 2035/106; G01N 30/74;
(Continued)

(56) References Cited

U.S. PATENT DOCUMENTS

| | | | |
|---|---|---|---|
| 2010/0178204 A1 | 7/2010 | Yin et al. | |
| 2013/0079236 A1* | 3/2013 | Holmes | G01N 33/50 506/9 |

FOREIGN PATENT DOCUMENTS

| | | | |
|---|---|---|---|
| JP | 2003-156498 A | 5/2003 | |
| JP | 2004-340969 A | 12/2004 | |

(Continued)

OTHER PUBLICATIONS

European Search Report of European application No. 14862749.0 dated Jul. 7, 2017.

*Primary Examiner* — Jennifer Wecker
(74) *Attorney, Agent, or Firm* — Revolution IP, PLLC

(57) ABSTRACT

Disclosed is an automatic in-vitro diagnosis method for increasing diagnostic reliability and a diagnosis speed by automatically mixing a specimen taken from the body of a person with a reagent in volumes needed to diagnose the state of the person using the specimen, absorbing the mixture solution of the reagent and the specimen with an analysis strip for a predetermined time, and making a diagnosis by analysis.

7 Claims, 7 Drawing Sheets

(51) Int. Cl.
*G01N 30/74* (2006.01)
*G01N 35/04* (2006.01)
*G01N 33/48* (2006.01)
*G01N 33/483* (2006.01)

(52) U.S. Cl.
CPC ....... *G01N 35/00722* (2013.01); *G01N 35/04* (2013.01); *G01N 35/10* (2013.01); *G01N 33/483* (2013.01); *G01N 35/1009* (2013.01); *G01N 35/1011* (2013.01); *G01N 2035/00108* (2013.01); *G01N 2035/00891* (2013.01); *G01N 2035/0491* (2013.01); *G01N 2035/106* (2013.01)

(58) Field of Classification Search
CPC .................. G01N 33/48; G01N 33/483; G01N 35/00029; G01N 35/00722; G01N 35/10; G01N 35/04; G01N 35/1011; G01N 35/1009; G01N 2035/0491
See application file for complete search history.

(56) References Cited

FOREIGN PATENT DOCUMENTS

| | | |
|---|---|---|
| JP | 2008-537119 A | 9/2008 |
| WO | 91/17446 A1 | 11/1991 |
| WO | 02/059563 A2 | 8/2002 |
| WO | WO-02059563 A2 * | 8/2002 ......... G01N 35/0099 |

* cited by examiner

METHOD FOR AUTOMATIC IN VITRO DIAGNOSIS

CROSS REFERENCE TO PRIOR APPLICATIONS

This application is a National Stage Application of PCT International Patent Application No. PCT/KR2014/009282 filed on Oct. 1, 2014, under 35 U.S.C. § 371, which claims priority to Korean Patent Application No. 10-2013-0140186 filed on Nov. 18, 2013, which are all hereby incorporated by reference in their entirety.

TECHNICAL FIELD

The present invention relates to an automatic in-vitro diagnosis method, and more particularly, to an automatic in-vitro diagnosis method for increasing diagnostic reliability and a diagnosis speed by automatically mixing a specimen taken from the body of a person with a reagent in volumes needed to diagnose the state of the person using the specimen, absorbing the mixture solution of the reagent and the specimen with an analysis strip for a predetermined time, and making a diagnosis by analysis.

BACKGROUND ART

In general, In-Vitro Diagnostics (IVD) is a diagnosis technique of taking a body fluid as a specimen, such as blood, urine, excrement, spinal fluid, various tissues, gastric fluid, or synovial fluid, from a human body and making a diagnosis by optically detecting chemical properties using a reagent reacting to the specimen.

Typically, a clinic makes an in-vitro diagnosis by extracting a necessary specimen from a human body, post-processing the extracted specimen, for example, by cultivation or separation in a laboratory, and diagnosing the specimen through interpretation using a magnifying tool such as a microscope or other analysis tools by a tester having medical knowledge. This in-vitro diagnosis technique takes expensive equipment and many personnel, thus increasing cost.

The in-vitro diagnosis technique is used to make a diagnosis of a specific disease or evaluate the state of a patient in a clinic by taking a specimen from the patient and testing the specimen in the departments of diagnostic medicine and pathology.

Recently, a specific reagent chemically reacting to an extracted specimen has been developed and an in-vitro diagnosis has been made by optically analyzing features resulting from chemical reaction between the specimen and the reagent in some diagnostic tests.

In such an in-vitro diagnosis, a material such as blood or urine is taken as a specimen from a human body, mixed with a reagent causing chemical reaction according to the type of the specimen and a diagnosis purpose, and analyzed by means of an analyzer. The in-vitro diagnosis is used for diagnosis such as immunological diagnosis, clinical diagnosis, clinical microbiological diagnosis, tissue diagnosis, molecular diagnosis, self-blood sugar metering, in-situ testing, and hemostasis testing.

In the in-vitro diagnosis technique as described above, a specimen suitable for a test is selected from materials taken from a human body, such as blood and urine, mixed with a reagent prepared according to the specimen and a test method, absorbed with an analysis strip, and diagnosed by means of a diagnostic device such as a laser beam-based fluorescent diagnostic device.

In the conventional in-vitro diagnosis device, however, an operator manually introduces and mixes a specimen and a reagent using a manual suction tool, pipette. Therefore, the volumes of the specimen and the reagent are different according to the skill of the operator and a task state, thereby decreasing diagnostic reliability.

Moreover, the mixture of the specimen and the reagent is dropped on an analysis strip formed of an absorbing material, and an analysis should be made after a predetermined time over which the mixture is absorbed into the analysis strop. However, the volumes of the dropped specimen and reagent may differ according to the skill of the operator and the task state, and it may take a different time to absolve the mixture with the analysis strip. As a result, diagnostic reliability is decreased significantly.

Since the specimen has been taken from the human body and thus is vulnerable to contamination or component transform with the passage of time due to external factors such as temperature, foreign materials, and humidity, a diagnosis should be made rapidly. However, a manual diagnosis may suffer time delay and thus contamination or component transform of the specimen, thereby decreasing the accuracy of a diagnosis result.

DISCLOSURE

Technical Problem

An object of the present invention devised to solve the conventional problem is to provide an automatic in-vitro diagnosis method for increasing diagnostic reliability and a diagnosis speed by automatically mixing a specimen taken from the body of a person to be diagnosed with a reagent, in accurate volumes, absorbing the mixture with an analysis strip for a predetermined time, and then making a diagnosis in order to diagnose the state of the person by means of the specimen.

It will be appreciated by persons skilled in the art that the objects that could be achieved with the present invention are not limited to what has been particularly described hereinabove and the above and other objects that the present invention could achieve will be more clearly understood from the following detailed description.

Technical Solution

In an aspect of the present invention, an automatic in-vitro diagnosis method for automatically performing a diagnosis by analyzing a specimen taken from a human body comprises providing a storage body to a housing, the storage body containing the specimen, a reagent to be mixed with specimen, an analysis strip, and a suction tip, and manipulating diagnosis operation on a manipulating a display unit connected to a controller by a user, mounting the suction tip of the storage body to a suction unit for applying suction pressure, the storage body being moved to a transfer unit according to a control signal of the controller upon the manipulation, moving the mounted suction tip to a position of the specimen, and sucking the specimen with the suction tip, moving the suction tip which suck the specimen to a position of the reagent, and mixing the specimen with the reagent through successive suction and discharge, dropping the mixture solution of the specimen and the reagent onto the analysis strip contained in the storage body, and removing the suction tip to the outside by allowing the suction tip to be caught in the transfer unit, while moving up and down the suction tip after the dropping, moving the analysis strip on which the mixture solution dropped to an analytic diagnosis unit for optically making an analytic diagnosis, and diagnosing and discharging the storage body to the outside by operating the transfer unit, after the diagnosis.

A use modes may be displayed on the manipulating display unit provided on one side surface of the housing, and the manipulating of a diagnosis operation may comprises, if the use mode is selected, transmitting a process signal corresponding to the selected use mode to the controller, and automatically performing the diagnosis operation.

The suction unit may be configured to move up and down, applying suction pressure to an upper part of the transfer unit, suck the specimen, mix the specimen with the reagent, and applies the suction pressure while moving up and down when the mixture solution is dropped onto the analysis strip.

The diagnosing step may comprises displaying the diagnosis result of the analytic diagnosis unit on the manipulating display unit provided on one side surface of the housing to enable a user to view the diagnosis result.

The diagnosing may comprises printing the diagnosis result of the analytic diagnosis unit on a sheet of paper through a printer provided on the housing.

The sucking of the specimen with the suction tip may comprises, after the suction tip is mounted to the suction unit and before the specimen sucked, when the suction tip is positioned at a position of the reagent stored in the storage body in a vacuum state by operating the transfer unit, moving down the suction tip and releasing the reagent from the vacuum state by puncturing.

The diagnosing may comprises measuring fluorescent and chemical luminosity or absorbance using chromatography analysis by the analytic diagnosis unit.

Details of other embodiments are incorporated in the detailed description and the drawings.

Advantageous Effects

According to an in-vitro diagnosis method according to an embodiment of the present invention, since a specimen taken from the body of a person to be diagnosed is automatically mixed with an reagent, in accurate volumes, the mixture is absorbed with an analysis strip for a predetermined time, and then a diagnosis is made, in order to diagnose the state of the person by means of the specimen, diagnostic reliability and a diagnosis speed can be increased.

Further, in the automatic in-vitro diagnosis method of the present invention, the reagent and the specimen to be mixed for diagnosis are supplied automatically accurately with accurate suction pressure, and mixed accurately by repeated suction and spraying. Therefore, the mixture solution of the reagent and the specimen is supplied at an accurate ratio in a volume needed for diagnosis, thereby increasing diagnostic reliability.

According to the automatic in-vitro diagnosis method of the present invention, the mixture solution of the reagent and the specimen is automatically dropped on an accurate position of the analysis strip and automatically supplied to an analytic diagnosis unit a predetermined time later. Therefore, as an accurate time is delayed to allow the analysis strip to absorb an accurate volume of the mixture solution dropped on the analysis strip, diagnostic reliability can be increased.

Also, since suction, mixing, dropping, and analytic diagnosis are performed automatically by sideways movement of a transfer unit and up and down movement of a suction unit which moves a specimen, a reagent, and an analysis strip to the transfer unit, applying suction pressure to them and which is supported inserted into a suction tip replaced at each diagnosis, the suction tip is replaced at each diagnosis and thus sanitary, and the automatic proceedings shorten a diagnosis time in the automatic in-vitro diagnosis method of the present invention. Accordingly, a diagnosis speed can be increased.

It will be appreciated by persons skilled in the art that the effects that can be achieved with the present invention are not limited to what has been particularly described hereinabove and other advantages of the present invention will be more clearly understood from the following detailed description taken in conjunction with the accompanying drawings.

BEST MODE FOR CARRYING OUT THE INVENTION

Figure 1:
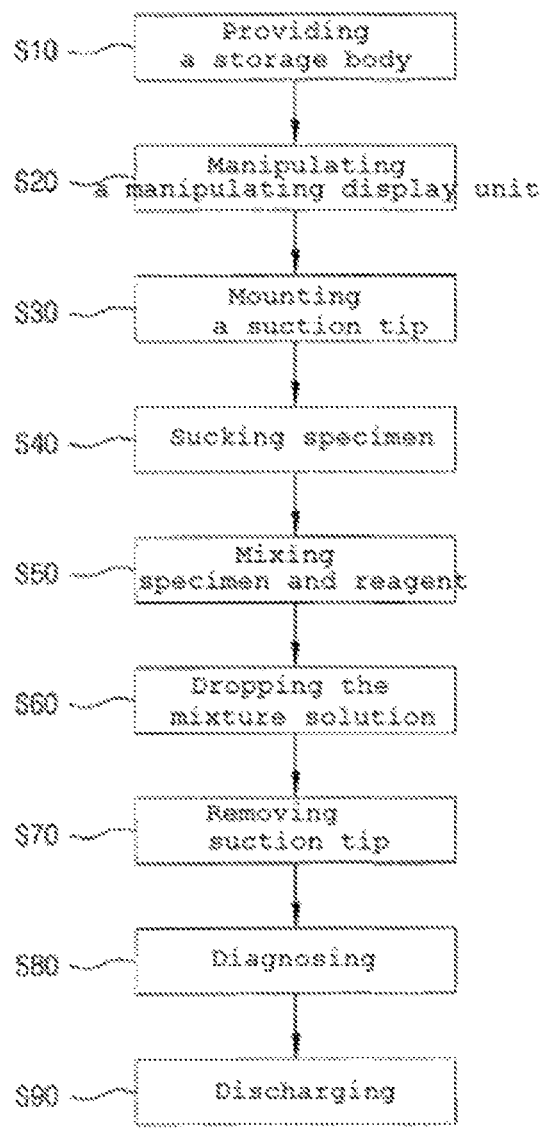
FIG. 1 is a flowchart illustrating an automatic in-vitro diagnosis method according to an embodiment of the present invention.

With reference to the attached drawings, a preferred embodiment of the present invention will be described in detail so that those skilled in the art may readily practice the present invention.

A description of technical contents which are known to the field of the present invention and have no direct relation to the present invention is omitted in the following description of the embodiment, lest it should not obscure the subject matter of the present invention.

For the same reason, some components are shown as exaggerated, omitted, or schematic in the attached drawings. Also, the size of each component does not match its actual size all the time. Like reference numerals denote the same or corresponding components in the drawings.

Now, a description will be given of an automatic in-vitro diagnosis method according to an embodiment of the present invention with reference to the attached drawings.

Figure 2:
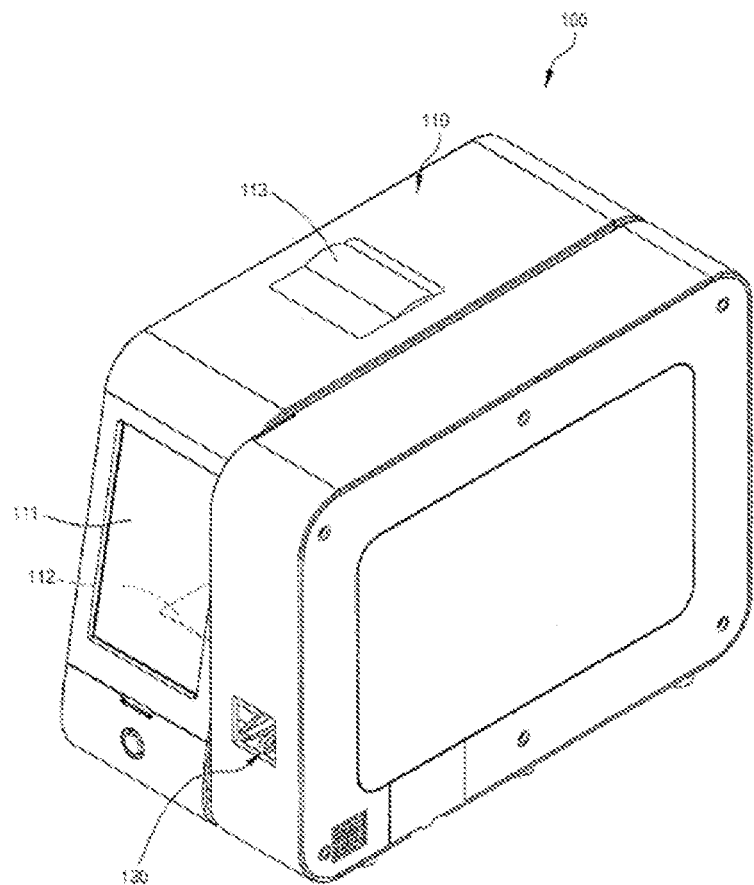
FIG. 2 is a perspective view illustrating an in-vitro diagnosis apparatus used for the automatic in-vitro diagnosis method illustrated in FIG. 1.
Figure 3:
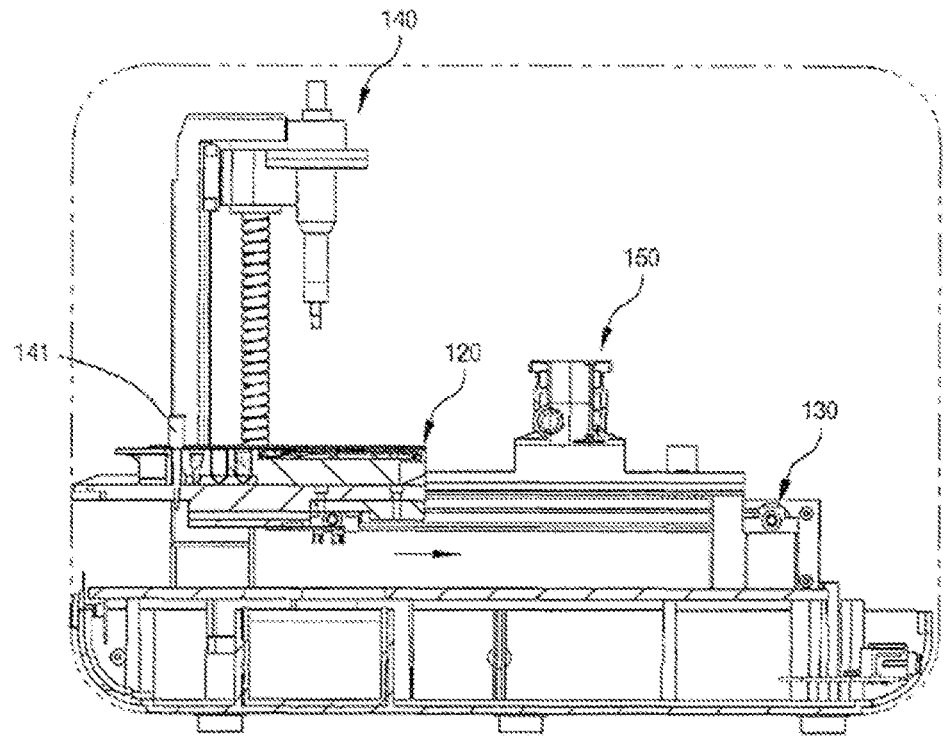
FIG. 3 is a use state diagram illustrating a state in which a storage body is provided and moved to a transfer unit in a storage body providing step of the automatic in-vitro diagnosis method illustrated in FIG. 1.
Figure 4:
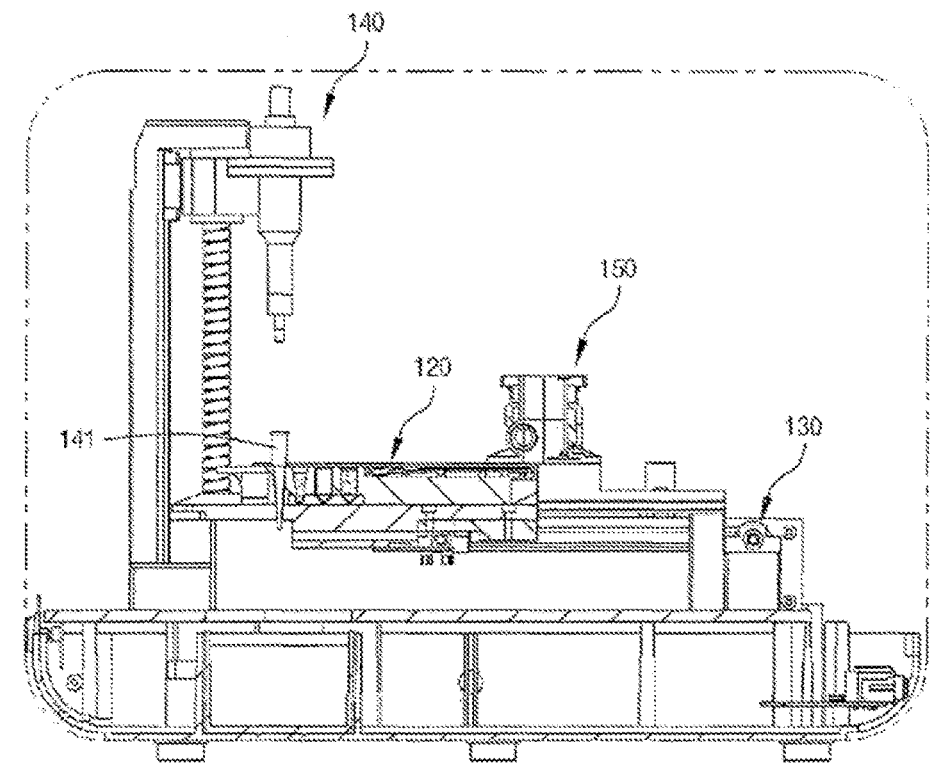
FIG. 4 is a use state diagram illustrating a state in which after the storage body is provided and moved to the transfer unit, a suction tip is positioned under a suction unit in the automatic in-vitro diagnosis method illustrated in FIG. 1.
Figure 5:
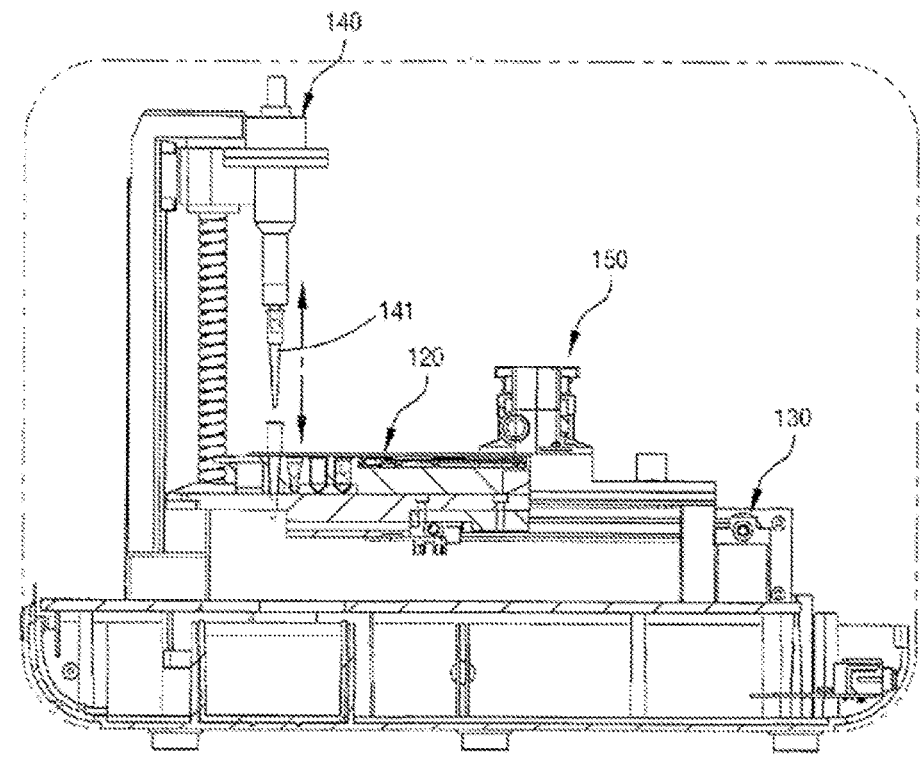
FIG. 5 is a use state diagram illustrating a state in which the suction tip is mounted in a suction tip mounting step of the automatic in-vitro diagnosis method illustrated in FIG. 1.
Figure 6:
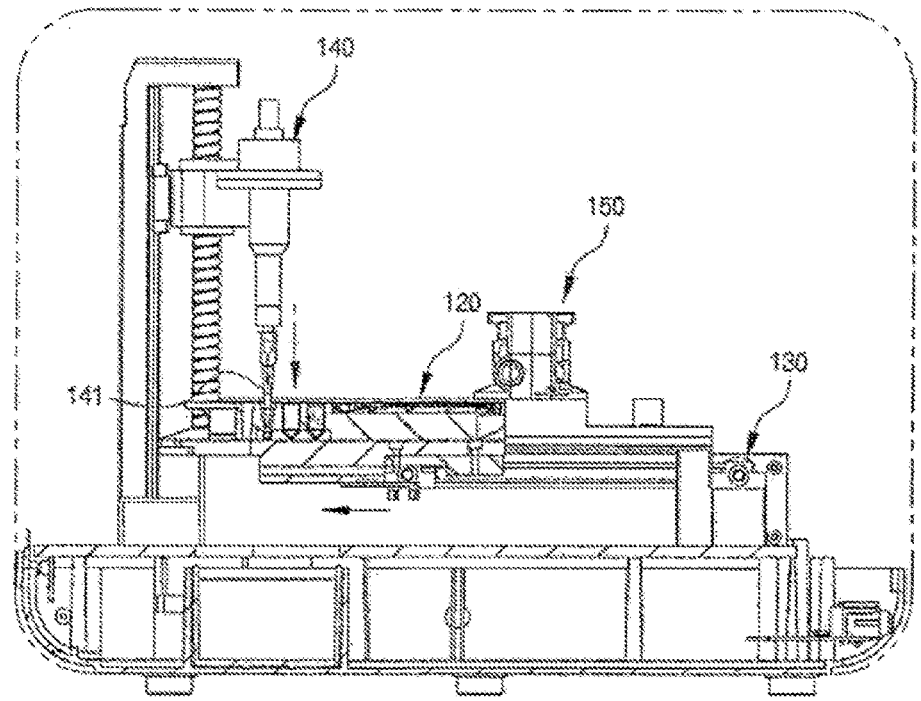
FIG. 6 is a use state diagram illustrating a state in which a specimen is sucked in a specimen suction step of the automatic in-vitro diagnosis method illustrated in FIG. 1.
Figure 7:
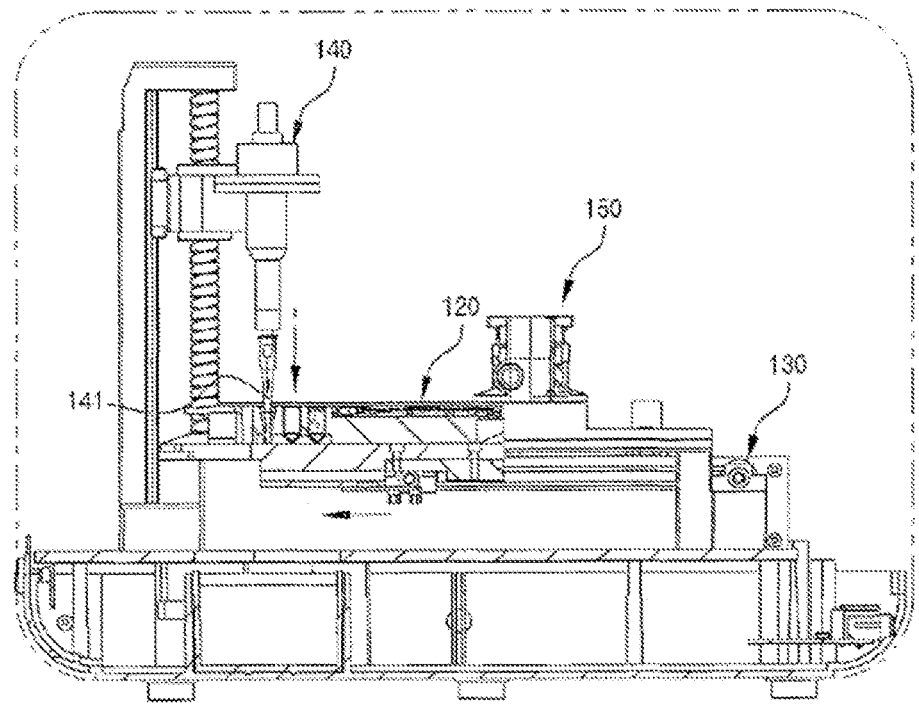
FIG. 7 is a use state diagram illustrating a state in which the specimen is mixed with a reagent in a specimen and reagent mixing step of the automatic in-vitro diagnosis method illustrated in FIG. 1.
Figure 8:
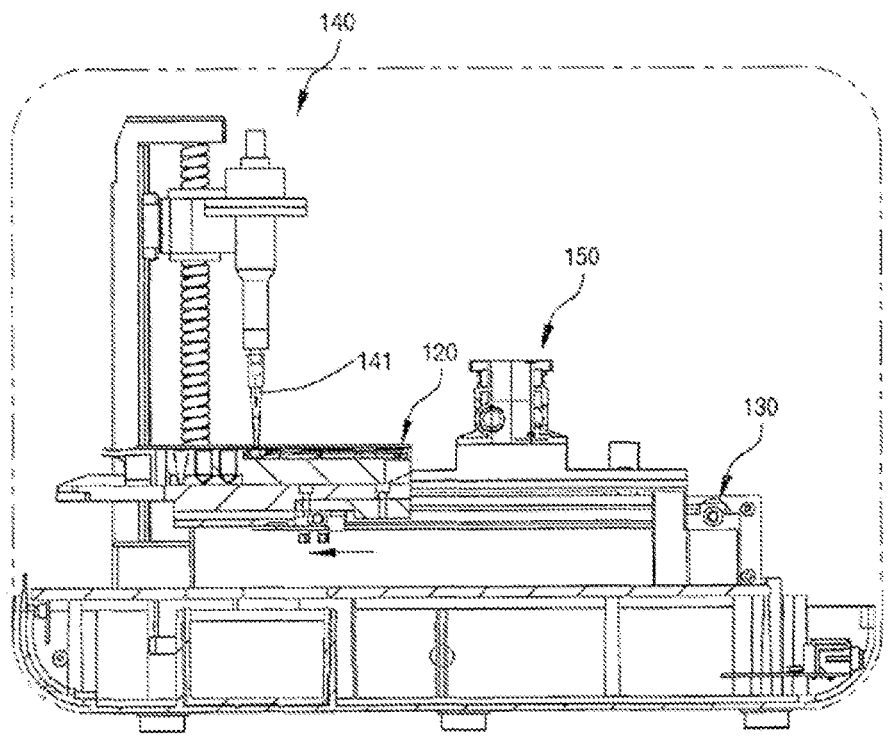
FIG. 8 is a use state diagram illustrating a state in which the mixture solution is dropped on an analysis strip in a mixture solution dropping step of the automatic in-vitro diagnosis method illustrated in FIG. 1.
Figure 9:
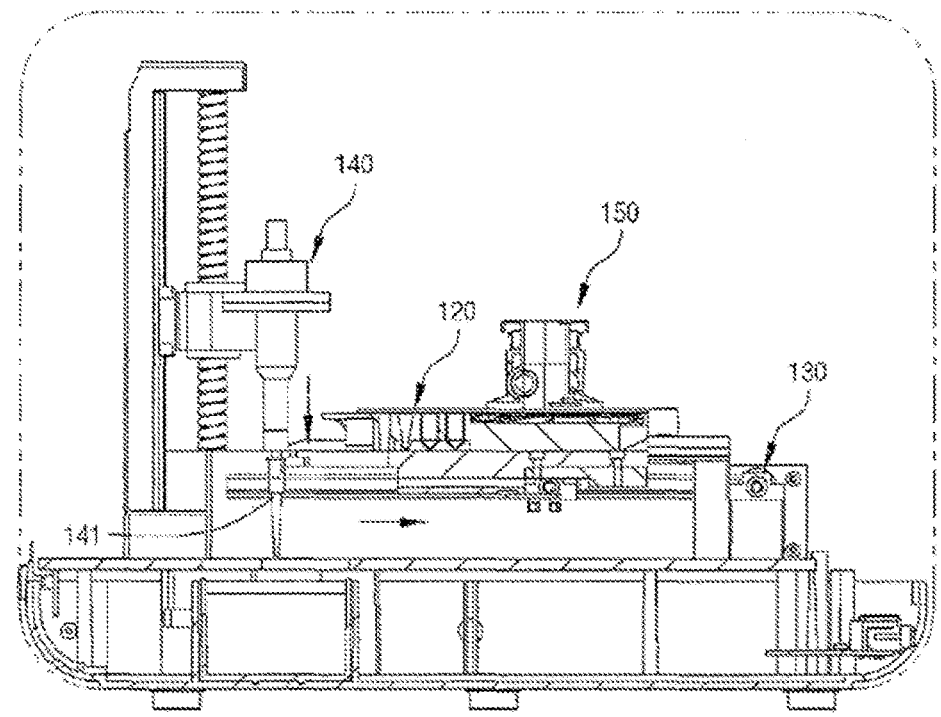
FIG. 9 is a use state diagram illustrating a state in which the suction tip moves down to a removal position in a suction tip removing step of the automatic in-vitro diagnosis method illustrated in FIG. 1.
Figure 10:
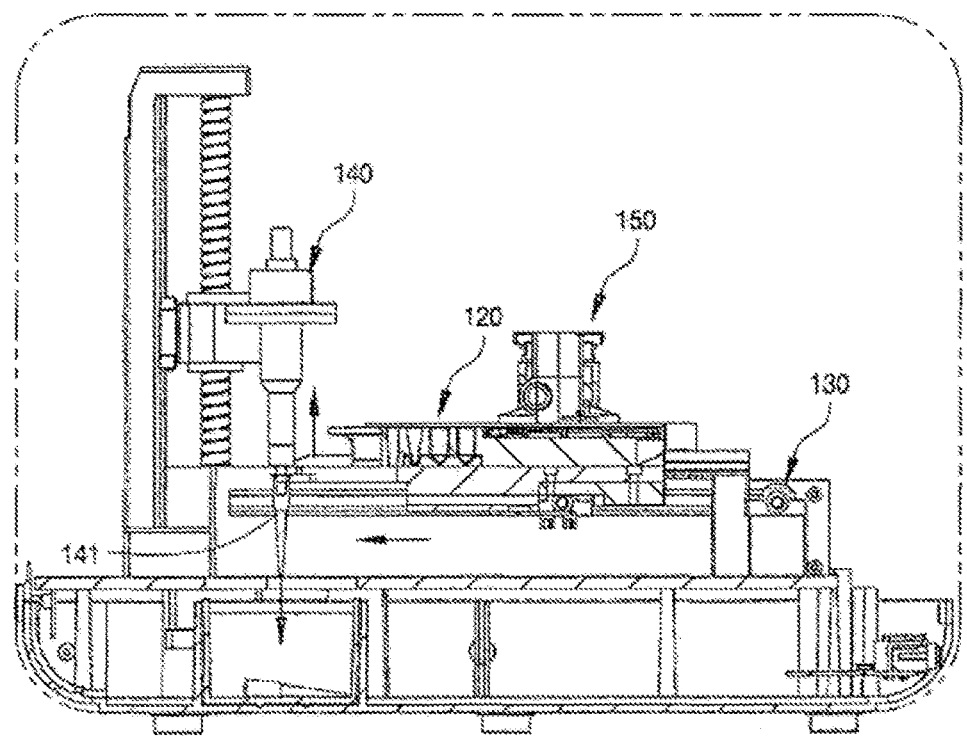
FIG. 10 is a use state diagram illustrating a state in which the suction tip is removed caught, while rising from the removal position in the suction tip removing step of the automatic in-vitro diagnosis method illustrated in FIG. 1.
Figure 11:
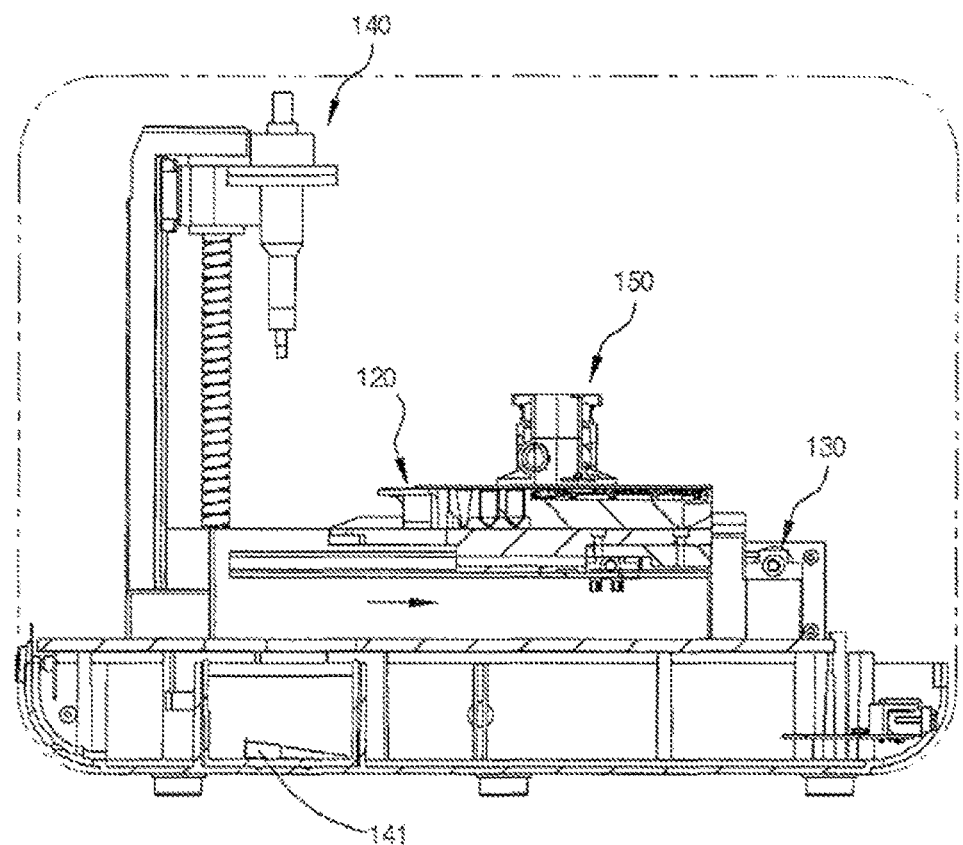
FIG. 11 is a use state diagram illustrating a state in which the storage body is supplied to an analytic diagnosis unit and a diagnosis is made in a diagnosis step of the automatic in-vitro diagnosis method illustrated in FIG. 1.

FIG. 1 is a flowchart illustrating an automatic in-vitro diagnosis method according to an embodiment of the present invention, FIG. 2 is a perspective view illustrating an in-vitro diagnosis apparatus used for the automatic in-vitro diagnosis method illustrated in FIG. 1, FIG. 3 is a use state diagram illustrating a state in which a storage body is provided and moved to a transfer unit in a storage body providing step of the automatic in-vitro diagnosis method illustrated in FIG. 1, FIG. 4 is a use state diagram illustrating a state in which after the storage body is provided and moved to the transfer unit, a suction tip is positioned under a suction unit in the automatic in-vitro diagnosis method illustrated in FIG. 1, FIG. 5 is a use state diagram illustrating a state in which the suction tip is mounted in a suction tip mounting step of the automatic in-vitro diagnosis method illustrated in FIG. 1, FIG. 6 is a use state diagram illustrating a state in which a specimen is sucked in a specimen suction step of the automatic in-vitro diagnosis method illustrated in FIG. 1, FIG. 7 is a use state diagram illustrating a state in which the specimen is mixed with a reagent in a specimen and reagent mixing step of the automatic in-vitro diagnosis method illustrated in FIG. 1, FIG. 8 is a use state diagram illustrating a state in which the mixture solution is dropped on an analysis strip in a mixture solution dropping step of the automatic in-vitro diagnosis method illustrated in FIG. 1, FIG. 9 is a use state diagram illustrating a state in which the suction tip moves down to a removal position in a suction tip removing step of the automatic in-vitro diagnosis method illustrated in FIG. 1, FIG. 10 is a use state diagram illustrating a state in which the suction tip is removed caught, while moving up from the removal position, in the suction tip removing step of the automatic in-vitro diagnosis method illustrated in FIG. 1, and FIG. 11 is a use state diagram illustrating a state in which the storage body is supplied to an analytic diagnosis unit and a diagnosis is made in a diagnosis step of the automatic in-vitro diagnosis method illustrated in FIG. 1.

Referring to FIGS. 1 to 11, in an automatic in-vitro diagnosis method according to an embodiment of the present invention, a bodily secretion such as urine or excrement discharged from a human body or a body fluid such as blood, spinal fluid, various tissues, gastric fluid, or synovial fluid, which does not do any harm to the human body during extraction and is reproducible, is taken as a specimen, the specimen is mixed with a reagent which causes a chemically analyzable reaction according to the type of the specimen and a diagnosis purpose, and the mixture solution is optically analyzed. In this manner, a diagnosis is made automatically.

The above-described automatic in-vitro diagnosis method comprises a step of providing a storage body (S10), a step of manipulating a manipulating display unit (S20), a step of mounting a suction tip (S30), a step of sucking a specimen (S40), a step of mixing a specimen and reagent (S50), a step of dropping a mixture solution (S60), a step of removing a suction tip (S70), a step of diagnosing (S80), and a step of discharging (S90).

In the step of providing storage body S10, a storage body 120 that accommodates a specimen, a reagent to be mixed with the specimen, an analysis strip, and a suction tip 141 is supplied to a housing 110.

With the specimen to be diagnosed, the reagent causing a chemical reaction to the specimen, and the analysis strip on which the mixture solution of the specimen and the reagent is dropped, for analysis, contained in the storage body 120, the storage body 120 is inserted into the housing 110 from one side of the housing 110.

In the step of manipulating a manipulating display unit S20, a user manipulates a manipulating display unit 111 connected to a controller 112, for a diagnosis operation.

After the storage body 120 is inserted, use modes are displayed on the manipulating display unit 111. Upon user selection of a use mode, a process signal corresponding to the selected use mode is transmitted to the controller 112, to thereby automatically perform the diagnosis operation.

There are a plurality of use modes having process signals to operate the controller 112 according to specimen types and diagnosis purposes. A process signal corresponding to a user-selected use mode is transmitted to the controller 112 so that the diagnosis operation may be automatically performed.

In the step of mounting suction tip S30, the suction tip 141 of the storage body 120 moved to a transfer unit 130 according to a signal of the controller 112 generated by manipulation is mounted to a suction unit 140 that provides suction pressure. The suction unit 140 moves up and down, applying the suction pressure to an upper part of the transfer unit 130.

As the transfer unit 130 is operated by the signal from the controller 112, the transfer unit 130 moves the suction tip 141 containing a solution in the storage body 120 to under the suction unit 140. The suction unit 140 moves down, fits into the suction tip 141, and moves up and down with the suction tip 141, applying suction pressure.

If after the suction tip 141 is mounted to the suction unit 140, the suction tip 141 is positioned above the position of a reagent stored in the storage body 120 in vacuum condition by operation of the transfer unit 130, the suction tip 141 moves down and releases the reagent from the vacuum state by puncturing.

In the step of sucking specimen S40, the suction tip 141 mounted to the suction unit 140 moves to the position of the reagent and sucks the reagent.

After the suction tip 141 is mounted to the suction unit 140, the suction tip 141 moves up along with upward movement of the suction unit 140, and the storage body 120 is moved by operation of the transfer unit 130 so that the reagent contained in the storage body 120 may be positioned under the suction tip 141. Then, the suction tip 141 moves down by operation of the suction unit 140 and sucks the reagent into it with suction pressure applied by the suction unit 140. Herein, the suction unit 140 applies the suction pressure at a level suitable for a used volume of the specimen according to a signal from the controller 112 so that an accurate volume of the specimen may be supplied.

In the step of mixing specimen and reagent S50, the suction tip 141 that has sucked the specimen in it moves to the position of the reagent and mixes the sucked specimen with the reagent by successive suction and discharge.

With the specimen sucked into the suction tip 141, the suction unit 140 moves up, and the storage body 120 is transferred by operation of the transfer unit 130 so that the suction tip 141 is positioned above the position of the reagent. Then, the suction tip 141 moves down along with operation of the suction unit 140 and mixes the contained specimen with the reagent by successive suction and discharge with suction pressure.

In the step of dropping mixture solution S60, the mixture solution of the specimen and the reagent is dropped on the analysis strip contained in the storage body 120.

With the mixture of the specimen and the reagent contained in the suction tip 141, the suction tip 141 moves up along with operation of the suction unit 140. Then, when the storage body 120 is transferred by operation of the transfer unit 130 so that the suction tip 141 may be positioned above a drop position of the analysis strip, the suction tip 141 moves down along with operation of the suction unit 140. If the suction tip 141 reaches the drop position of the analysis strip, the suction tip 141 drops the mixture solution onto the analysis strip along with release of the suction pressure.

In the step of removing suction tip S70, the suction tip 141, which has dropped the mixture solution, moves up and down. During the up and down movement, the suction tip 141 is caught in the transfer unit 130 and thus removed to the outside.

After the suction tip 141 finishing dropping the mixture solution moves up, the transfer unit 130 moves to the other side. Subsequently, the suction tip 141 moves down to a position at which it will be caught in an end of the transfer unit 130, and the transfer unit 130 moves to a side at which the suction tip 141 will be caught. Then, the suction tip 141 moves up and is caught in the transfer unit 130. Thus, the suction tip 141 is removed down.

In the step of diagnosing S80, the analysis strip having the mixture solution dropped on it is moved to an analytic diagnosis unit 150 that optically makes an analytic diagnosis, by operation of the transfer unit 130.

Preferably, the analytic diagnosis unit 150 measures fluorescent and chemical luminosity or absorbance by chromatography analysis.

Further, the manipulating display unit 111 provided on a side surface of the housing 110 may display a diagnosis result of the analytic diagnosis unit 150 so that the user may view the diagnosis result.

The diagnosis result of the analytic diagnosis unit 150 may be printed onto a sheet of paper by a printer 113 provided on the housing 110.

After the suction tip 131 is removed, the analysis strip into which the mixture solution has been absorbed is transferred to the analytic diagnosis unit 150 for optical analysis, and then an analytic diagnosis is made. After the diagnosis, a diagnosis result may be displayed as an image on the manipulating display unit 111 or output on a sheet of paper through the printer 113.

In the discharge step S90, upon completion of the diagnosis and analysis, the storage body 120 is discharged to the outside by operation of the transfer unit 130.

After the diagnosis, the storage body 120 is discharged by operation of the transfer unit 130. Thus, the test is finished.

The preferred embodiment of the present invention has been described and illustrated in the present disclosure and the drawings. While specific terms are used, these terms are provided in general meanings in order to easily describe the technical aspects of the present invention and help the understanding of the present invention, not intended to limit the scope of the present invention. Accordingly, it is apparent to those skilled in the art that other modification examples can be implemented without departing from the scope of the present invention, in addition to the disclosed embodiment of the present invention.

INDUSTRIAL APPLICABILITY

Since a specimen taken from a human body is automatically mixed with a reagent in accurate volumes, the mixture is absorbed with an analysis strip for a predetermined time, and then a diagnosis is made in order to diagnose the state of a person to be diagnosed with the specimen, the automatic in-vitro diagnosis method increases diagnostic reliability and a diagnosis speed. Therefore, the automatic in-vitro diagnosis method is useful in the in-vitro diagnosis industry.

The invention claimed is:

1. An automatic in-vitro diagnosis method for automatically performing a diagnosis by analyzing a specimen taken from a human body, the method comprising:
    providing a storage body to a housing, the storage body containing the specimen, a reagent to be mixed with specimen, an analysis strip, and a suction tip, and manipulating a diagnosis operation by having a user manipulate a display unit connected to a controller;
    mounting the suction tip of the storage body to a suction unit for applying suction pressure, the storage body being moved to a transfer unit according to a control signal of the controller upon the manipulation, and moving the mounted suction tip to a position of the specimen, and sucking the specimen with the suction tip;
    moving the suction tip, which sucks the specimen, to a position of the reagent, and mixing the specimen with the reagent through successive suction and discharge; dropping the mixture solution of the specimen and the reagent onto the analysis strip contained in the storage body, and removing the suction tip to the outside by allowing the suction tip to be caught in the transfer unit, while moving the suction tip up and down after the mixture solution is dropped;
    moving the analysis strip on which the mixture solution is dropped to an analytic diagnosis unit for optically making an analytic diagnosis, and diagnosing; and
    discharging the storage body to the outside by operating the transfer unit, after the diagnosis.

2. The automatic in-vitro diagnosis method according to claim 1, wherein a use mode is displayed on the manipulated display unit provided on one side surface of the housing, and manipulating a diagnosis operation comprises, if the use mode is selected, a process signal corresponding to the selected use mode is transmitted to the controller, and the diagnosis operation is automatically performed.

3. The automatic in-vitro diagnosis method according to claim 1, wherein the suction unit is configured to move up and down, applying suction pressure to an upper part of the transfer unit, sucking the specimen, mixing the specimen with the reagent, and applying the suction pressure while moving up and down when the mixture solution is dropped onto the analysis strip.

4. The automatic in-vitro diagnosis method according to claim 1, wherein the diagnosing comprises displaying the diagnosis result of the analytic diagnosis unit on the manipulated display unit provided on one side surface of the housing to enable a user to view the diagnosis result.

5. The automatic in-vitro diagnosis method according to claim 1, wherein the diagnosing comprises printing the diagnosis result of the analytic diagnosis unit on a sheet of paper through a printer provided on the housing.

6. The automatic in-vitro diagnosis method according to claim 1, wherein the sucking of the specimen with the suction tip comprises, after the suction tip is mounted to the suction unit and before the specimen is sucked, positioning the suction tip at a position of the reagent stored in the storage body in a vacuum state by operating the transfer unit, moving down the suction tip and releasing the reagent from the vacuum state by puncturing.

7. The automatic in-vitro diagnosis method according to claim 1, wherein the diagnosing comprises measuring a fluorescent and chemical luminosity or absorbance using chromatography analysis by the analytic diagnosis unit.

* * * * *